United States Patent [19]

Murmann et al.

[11] 4,358,441
[45] Nov. 9, 1982

[54] NICOTINIC DERIVATIVES OF GLUCOSAMINE AND RELATED PHARMACEUTICAL COMPOSITIONS

[75] Inventors: Walter Murmann, Arona; Osvaldo Ponchiroli, Rho Milano, both of Italy

[73] Assignee: Laboratorio Guidotti & C. S.p.A., Pisa, Italy

[21] Appl. No.: 265,348

[22] Filed: May 19, 1981

[30] Foreign Application Priority Data

May 20, 1980 [IT] Italy ............................ 22188 A/80

[51] Int. Cl.$^3$ .................... A61K 31/70; C07H 5/06
[52] U.S. Cl. ................................. 424/180; 536/53
[58] Field of Search .................. 536/18, 53; 424/180

[56] References Cited

U.S. PATENT DOCUMENTS 3,934,009 1/1976 Gey et al. ............................ 536/53
3,950,324 4/1976 Gey et al. ............................ 536/53

FOREIGN PATENT DOCUMENTS 1166818 11/1958 France .
2258861 8/1975 France .

OTHER PUBLICATIONS

Jones et al., Chem. Abstracts, vol. 48, 1251h (1954).
Micheel et al., Chem. Abstracts, vol. 50, 11955h, (1956).

Primary Examiner—John M. Ford
Assistant Examiner—Bernard Dentz
Attorney, Agent, or Firm—McAulay, Fields, Fisher, Goldstein & Nissen

[57] ABSTRACT

The nicotinic derivatives of glucosamine, particularly N-nicotinoyl-glucosamine tetranicotinate are described as having anti-lipolitic, hypocholesterolemizing and antiaterogenic activities, at an equal or higher level than those of nicotinic acid, without the objectionable side effects shown by the acid. To prepare the compounds of the invention, nicotinoyl chloride hydrochloride and glucosamine hydrochloride are reacted in an organic solvent at a temperature of between 40° C. and 120° C.

7 Claims, No Drawings

NICOTINIC DERIVATIVES OF GLUCOSAMINE AND RELATED PHARMACEUTICAL COMPOSITIONS

FIELD OF THE INVENTION

The present invention relates to nicotinic derivatives of glucosamine and, more specifically, to glucosamine nicotinates, having the formula:

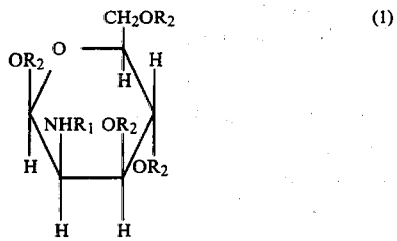

wherein $R_1$ is H or a nicotinic acid radical of the formula:

and $R_2$ represents the radical of the nicotinic acid.

More specifically the present invention relates to the N-nicotinoyl-glucosamine tetranicotinate having formula (1) in the isomeric forms α and β, the glucosamine tetranicotinate and their salts with non-toxic and pharmacologically acceptable acids, such as fumaric, tartaric, hydrochloric, phthalic and terephthalic acids.

It is known, since long time, that nicotinic acid is one of the most efficacious hypolipemizing agents, this action being supplemented by a hypocholesterolemizing effect and consequently by an anti-aterogenic activity. The acid, however, presents problems in its therapeutic use, both because it is very readily eliminated from the blood, and because at the high dosages needed to maintain an acceptable plasma content, undesirable and not negligible side effects occur, such as for instance the so-called "rebound" effect of the free fatty acids (FFA) and of free glycerol in the blood.

Such an effect is accompanied by toxic effects, at the hepatic level mainly, due to a lipidic infiltration of the lever, with prevailing accumulation of the triglyceride fraction. In recent years some derivatives of nicotinic acid, such as for example D-glucitol hexanicotinate, have been discovered and therapeutically used.

In this case the side effects can be substantially reduced, but the problem of the duration of the therapeutic effect after administration remains essentially unchanged.

If account is taken of the fact that these drugs are used for long term therapies or even for prevention treatments, the importance of less frequent administrations, affording the same therapy is evident.

SUMMARY OF THE INVENTION

It has been now found that the above mentioned problems, caused by nicotinic acid and its presently known derivatives, are substantially eliminated with the novel nicotinic derivatives of the present invention and more specifically with the glucosamine pentanicotinate.

By the term: "nicotinic derivatives of glucosamine" is meant the pentanicotinic ester of glucosamine in its isomeric forms α and β having formula (1), the tetranicotinic ester of glucosamine and its salts with non toxic and pharmaceutically acceptable acids, which hereinafter shall be considered as falling within the scope of the invention, even when reference is made only to the glucosamine pentanicotinate.

The following compounds are preferred:

(1) α-N-nicotinoyl-glucosamine tetranicotinate, having the structural formula (1) and the empirical formula $C_{30}H_{28}O_{10}N_6$; it is a white-ivory powder, having molecular weight 704.6 and melting point 158°–160° (with dec.), $[\alpha]_D^{20} = +119°$.

The compound is soluble in the common non-polar organic solvents, and the corresponding salts are water soluble.

Thin layer chromatographic analysis gives only one spot having Rf=0.4. β-N-nicotinoyl-glucosamine tetranicotinate, also of formula (1) is a solid, crystalline, white product, which is slightly soluble in acetone, ethanol and chloroform, but soluble in dilute acids.

(2) Its melting point ranges 198°–202° C., and $[\alpha]_D^{20} = -2.0°$ (5% solution in 1 N HCl).

(3) Glucosamine tetranicotinate having the formula:

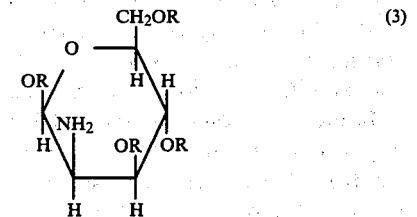

It is a crystalline, white product, soluble in the common organic solvents and in acid solutions, with a melting point 98° (with dec.) and $[\alpha]_D^{20} = +70°$ (5% solution in 1 N HCl).

The process according to the invention for the preparation of the pentanicotinic ester of glucosamine comprises the reaction in an organic solvent, particularly pyridine, of nicotinoyl chloride hydrochloride and glucosamine hydrochloride at a temperature of between 40° C. and 120° C. for a time of 1 to 20 hours, the reaction product being thereafter separated and purified.

More specifically, it has been found that by the process as above defined a mixture of the two isomers is obtained, the related proportions of which in the resulting reaction mixture vary depending on the reaction conditions and particularly depending upon the reaction temperature and time.

It has been found also that when the temperature and the time of the reaction are increased, within the previously indicated limits, the percentage of beta isomer increases and the percentage of alpha isomer correspondingly decreases.

Glucosamine tetranicotinate is obtained by hot acidic hydrolysis of pentanicotinate, both from the alpha and from the beta isomer. No isomeric forms of tetranicotinate have been detected.

The particular features of the process of the invention shall more clearly appear from the following examples.

EXAMPLE 1

The reaction takes place according to the following equation:

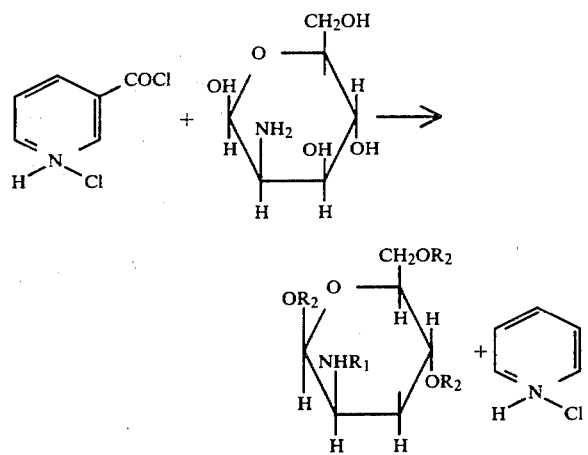

wherein both $R_1$ and $R_2$ represent a radical of nicotinic acid.

In a flask, provided with a stirrer, 550 mls of pyridine are charged and 75 g (0.49 moles) of nicotinoyl chloride hydrochloride are added in portions and with vigorous stirring; the reaction is exothermic and is carried out by cooling with an ice bath at a temperature of 15° C.

To the resulting mixture is added 17.6 g (0.082 moles) of glucosamine hydrochloride in crystalline form, having the following chemical and physical properties: m.p.=190°–194° C.; molecular weight=215.64; $[\alpha]_D^{20} = +82.4°$.

The reaction mass is heterogeneous and is slowly heated in a water bath, at a temperature of 70° C. for about 14 hours. At the end the reaction mass is homogeneous and is of brick-red colour.

The reaction mixture is cooled to room temperature, is filtered under vacuum from the thus formed pyridine hydrochloride, the filtrate is concentrated, added with 1 liter water and extracted twice with 300 mls of chloroform. At this point the separation of the two phases is carried out, the organic phase being then recovered, dried over sodium sulfate and concentrated under vacuum.

A spongy, tobacco coloured product is obtained, which is taken up with water and hydrogen chloride.

A cloudy solution results, which is buffered with diluted ammonia up to incipient precipitation; decolorizing charcoal is added and the solution is filtered.

The resulting clear solution is further decolorizing by adding more charcoal; the operation is repeated several times until a straw-coloured solution (500 mls) is obtained.

The aqueous solution is extracted with vigorous stirring with 300 mls of chloroform after alkalinization with diluted ammonia; two phases are separated, the organic phase being dried over sodium sulfate and concentrated under vacuum.

A white-ivory product is thus recovered which is crystallized from mixtures of alcohols and esters, with an 80% yield, the analytical composition comprising 87 to 93% of alpha isomer and 7 to 12% of beta isomer, and the melting point being 156° to 160° C.; 22 g of product are obtained, (corresponding a yield of 38.1% of theoretical value).

From the mixture the two isomers can be isolated by fractional crystallization.

EXAMPLE 2

In a flask, provided with a stirrer, 110 g of nicotinoyl chloride hydrochloride, 100 mls of pyridine, 500 mls of a 1:1 mixture of 1,1,1-trichloroetane and chloroform are charged, and the mixture is stirred until a single phase is obtained.

19 g of glucosamine hydrochloride are added at room temperature and the reaction mixture is heated for a time of 4 hours at a temperature of between 80° C.

The reaction mixture is evaporated under vacuum until dry, the mass is dispersed in water, extracted with chloroform, the organic phase being then dried.

There is thus obtained the desired product, $\beta$-N-nicotinoyl-glucosamine tetranicotinate, which upon crystallization from dimethylformamide-water is a white crystalline solid; the yield is 50–55%.

EXAMPLE 3

In a flask, provided with a stirrer, 50 g of $\beta$-N-niotinoyl-glucosamine tetranicotinate are dissolved in 2 liters of 0.5% HCl and heated to a temperature of 50° C. for 4 hours.

The solution is made alkaline with 5% sodium carbonate and extracted with 400 mls of chloroform; by evaporating the chloroformic solution a residue is obtained which, upon crystallization from acetone, gives a white crystalline powder (60% yield).

Using similar procedures, starting with 50 g of $\beta$-N-nicotinoyl-glucosamine tetranicotinate and 1% HCl, and by heating for 4 hours at 60° C., the same glucosamine tetranicotinate is obtained with a 65% yield.

For the preparation of the salts with non toxic and pharmacologically acceptable salts, the standard procedures for such a reaction are followed organic solvents, such as alcohols, dioxane and ketones being used, and temperatures not higher than 40° C., taking it into account that the conversion to the salt is complete.

The compounds of the present invention have been the subject of preliminary pharmacological tests, by which the previously mentioned properties have been shown.

As regards the toxicity it is to considered that the nicotinic acid, besides being part of all the living cells, has been used worldwide for about 25 years in the therapy of several pathological states, with the only limitation of the undesirable side effects, at dosages of between 1 and 10 g per day, and consequently its safety needs not to be confirmed by extended pharmacological experiments. Like considerations can be drawn as regards the glucosamine.

The preceeding conclusions have been confirmed by some practical tests, the results of which are reported in the table 1, only as regards the mixture of isomers and as obtained according to the example to the example 1 (the ratio between the isomers being 75 to 25) and which, for sake of brevity shall be indicated hereinafter with the abbreviation GLUN.

TABLE 1

Toxicity of GLUN, in comparison with nicotinic acid, in the rats of both sexes, by oral and intraperitoneal route

| COMPOUND | SEX | ADMINISTRATION ROUTE | $LD_{50}$ mg kg$^{-1}$ | RELIABILITY LIMITS AT 95% |
|---|---|---|---|---|
| GLUN | M | os | >8000 | — |
|  | F | os | >8000 | — |
| NICOTINIC ACID | M | os | 3860 | 3299–4516 |
|  | F | os | 3850 | 3441–4308 |
| GLUN | M | i.p. | 6650 | 6051–7308 |
|  | F | i.p. | 6750 | 6244–7297 |
| NICOTINIC ACID | M | i.p. | 328 | 301–357 |
|  | F | i.p. | 296 | 264–331 |

TABLE 2

Effect of oral administration of nicotinic acid, sorbinicate, niceritrole and GLUN at the dose of 100 mg/kg referred to nicotinic acid, on the plasma levels of FFA, free glyceral triglycerides and cholesterol in the empty rat.
Percent variations with respect to the controls (n = 5)

| | FFA | | | | | | | FREE GLYCEROL | | | | | | |
|---|---|---|---|---|---|---|---|---|---|---|---|---|---|---|
| TIME FROM THE ADMINISTRATION (h) | 2 | 4 | 6 | 8 | 10 | 16 | 24 | 2 | 4 | 6 | 8 | 10 | 16 | 24 | 32 |
| NICOTINIC ACID | −77 ••• | −68 ••• | +23 * | +23 •• (1) | +13 (1) | −9 (1) | −5 (1) | −73 ••• | −71 • | +9 | +11 (1) | +16 (1) | −12 (1) | −4 (1) |
| SORBINICATE | −72 ••• | −1 | +6 | +4 (1) | −5 (1) | +6 (2) | +2 (1) | −70 ••• | −3 | +3 | +20 * (1) | +8 (1) | −1 (1) | −1 (1) |
| NICERITROLE | −70 ••• | −43 * | +27 ** | +10 * (1) | −2 (1) | +6 (1) | −8 (1) | −61 ••• | −34 | +17 | +11 (1) | +4 (1) | +13 (1) | +3 (1) |
| GLUN | −74 ••• | −41 •• | −28 ** | −43 ••• (1) | −40 ••• (3) | −7 (1) | −2 (1) | −81 ••• | −47 * | −24 * | −32 ••• (1) | −41 •• (3) | +3 (1) | 0 (1) | +16 |

| | TRIGLYCERIDES | | | | | | | | CHOLESTEROL | | | | | | |
|---|---|---|---|---|---|---|---|---|---|---|---|---|---|---|---|
| TIME FROM THE ADMINISTRATION (h) | 2 | 4 | 6 | 8 | 10 | 16 | 24 | 32 | 4 | 6 | 8 | 10 | 16 | 24 | 32 | 48 |
| NICOTINIC ACID | −57 •• | −58 •• | −59 ••• | −38 ** (1) | +4 (1) | +21 (1) | −16 ** (1) | | −12 • | −12 • | −13 (1) | −17 (1) | −14 (1) | −27 •• (1) | | |
| SORBINICATE | −61 •• | −46 •• | −55 ••• | −5 (1) | +9 (1) | −3 (1) | −25 (1) | | −14 (4) | −15 (1) | −7 ** (1) | −15 (1) | −13 (1) | −9 (1) | | |
| NICERITROLE | −41 * | −56 •• | −63 ••• | −30 (1) | +9 (1) | −3 (1) | +5 (1) | | −2 | −7 | 0 | −10 | −17 | −14 * | | |
| GLUN | −52 •• | −65 ••• | −72 ••• | −75 ••• (1) | −65 ••• (3) | −67 •• (1) | 3 (1) | +13 | +9 | −4 | −13 * (1) | −29 ••• (3) | −53 ••• (1) | −37 ••• (1) | −42 •• | −29 • (5) |

* $P < 0.10$
** $P < 0.05$
• $P < 0.02$
•• $P < 0.01$
••• $P < 0.001$
(1) n = 10
(2) n = 9
(3) n = 17
(4) n = 4
(5) n = 6

TABLE 3

Effect of oral administration of nicotinic acid, sorbinicate, niceritrole and GLUN at the dose of 30 mg/kg referred to nicotinic acid, on the plasma levels of FFA, free glyceral triglycerides and cholesterol in the empty rat.
Percent variations with respect to the controls (n = 5)

| | FFA | | | | FREE GLYCEROL | | | | | | |
|---|---|---|---|---|---|---|---|---|---|---|---|
| TIME FROM THE ADMINISTRATION (h) | | | | | | | | | | | |
| COMPOUND | 1 | 2 | 4 | 6 | 1 | 2 | 4 | 6 | 8 | 10 | 12 | 16 |
| NICOTINIC ACID | −81 ••• | −43 ** | +23 (1) | +11 | −72 ••• | −27 | +16 (1) | +15 | | | | |
| SORBINICATE | −56 ** | −14 | +13 | −9 | −59 ••• | −27 * | +2 | −7 | | | | |

TABLE 3-continued

Effect of oral administration of nicotinic acid, sorbinicate, niceritrole and GLUN at the dose of 30 mg/kg referred to nicotinic acid, on the plasma levels of FFA, free glyceral triglycerides and cholesterol in the empty rat.
Percent variations with respect to the controls (n = 5)

| | | | (1) | | | | (1) | | | | |
|---|---|---|---|---|---|---|---|---|---|---|---|
| NICDRITROLE | −87 ••• | −18 | +9 | +8 | −77 ••• | −9 | −4 | +11 | | | |
| | | | (1) | | | | (1) | | | | |
| GLUN | −33 * | −67 ••• | −3 | −16 | −27 | −63 •• | −7 | −17 | −25 * | −4 | −5 | +5 |
| | | | (1) | | | | (1) | (1) | | (1) | |

| | | TIME FROM THE ADMINISTRATION (h) TRICLYCERIDES | | | | | | | |
|---|---|---|---|---|---|---|---|---|---|
| COMPOUND | | 1 | 2 | 4 | 6 | 8 | 10 | 12 | 16 |
| NICOTINIC ACID | | −49 • | −49 ••• | +8 (1) | +17 | | | | |
| SORBINICATE | | −42 ** | −16 | +6 (1) | −3 | | | | |
| NICDRITROLE | | −45 ** | −27 | +13 (1) | −6 | | | | |
| GLUN | | −2 | −45 •• | −44 •• (1) | −41 ** (1) | −36 ** | −62 ** | −31 ** (1) | +31 |

* P < 0.10
** P < 0.05
• P < 0.02
•• P < 0.01
••• P < 0.001
(1) n = 10
(2) n = 9

TABLE 4

Plasma levels of free nicotinic acid after administration of nicotinic acid, sorbinicate, niceritrole and GLUN at the dose of 100 mg/kg p.o. referred to nicotinic acid in the rat.
Average values ± standard (n = 4)

| COMPOUND | DOSE mg kg$^{-1}$ | FREE NICOTINIC ACID time from administration (h) | | | | | $\mu$g ml$^{-1}$ (h) | | |
|---|---|---|---|---|---|---|---|---|---|
| | | 0.5 | 1 | 2 | 4 | 6 | 8 | 12 | 16 |
| NICOTINIC ACID | 100 | 108.05 ±15.20 | 105.59 ±4.05 | 98.30 ±12.60 | 10.58 ±3.74 | 0.76 ±0.16 | 0.25 ±0.05 | 0.49 ±0.32 | 0.12 ±0.04 |
| SORBINI-CATE | 100 | 6.69 ±0.55 | 2.82 ±0.81 | 1.66 ±0.06 | 1.31 ±0.06 | 0.75 ±0.08 | 0.72 ±0.13 | 0.72 ±0.29 | 0.13 ±0.07 |
| NICERI-TROLE | 100 | 50.16 ±11.89 | 31.79 ±6.82 | 21.99 ±3.51 | 1.37 ±0.03 | 0.63 ±0.11 | 0.23 ±0.06 | 0.28 ±0.09 | 0.30 ±0.13 |
| GLUN | 100 | 0.96 ±0.09 | 1.25 ±0.06 | 1.96 ±0.31 | 2.07 ±0.52 | 1.57 ±0.17 | 1.76 ±0.11 | 2.63 ±0.74 | 1.35 ±0.25 |

As it can be seen from table 1, the acute toxicity of GLUN in the rat is negligible and 2 times lower by oral route and 20 times lower by intraperitoneal route than that of the nicotinic acid.

There have also been investigated the effects of the oral administration of glucosamine pentanicotinate (GLUN) on the plasma levels of free fatty acids, free glycerol, triglycerides and cholesterol in the empty rat, in comparison with like doses of nicotinic acid, sorbinicate (D-glucitol hexanicotinate) and niceritrole (penta-erithritol-tetranicotinate).

The kinetics of the free nicotinic acid in the plasma has been evaluated after an oral administration of GLUN, always in comparison with like doses of nicotinic acid, sorbinicate and niceritrole.

636 COBS CD (SD) BR male rats have been used in the whole, aged between 41 and 64 days and of body weight of between 180 and 345 grams.

The results are reported in the tables 2 (effects on plasma lipids at the dose of 100 mg/kg), 3 (effects on the plasma lipids at the dose of 30 mg/kg) and 4 (kinetics of the free nicotinic acid at the dose of 100 mg/kg). From the tables 2, 3 and 4, the following features appear evident:

(1) FFA

At the dose of 100 mg/kg the maximum anti-lipolitic effect occurs within 2 hours from the administration for all the four substances under test. The intensity of the maximum effect is practically the same, but the duration of the effect is different in the several groups.

The effect of the sorbinicate disappears within 4 hours, that of the nicotinic acid and of niceritrole within 6 hours, and that of GLUN within 16 hours. A FFA rebound is induced by nicotinic acid and niceritrole at the eighth and sixth hour respectively, whereas sorbinicate and GLUN do not show this effect.

At a dosage of 30 mg.kg the four substances under test depress the plasma FFA after 1 hour, but only GLUN is still active in the second hour. The nicotinic acid only causes FFA rebound in the fourth hour.

(2) Free glycerol

The effects of tested compounds on free glycerol are roughly identical to those on FFA at a dosage of 100 mg/kg. The maximum effect is detected for all the substances within the second hour. The effect of the sorbinicate and of niceritrole disappears within the fourth hour, that of the nicotinic acid within the sixth hour, that of GLUN within the sixteenth hour.

At the dose of 30 mg/kg nicotinic acid, sorbinicate, and niceritrole are active only after 1 hour, whereas GLUN is active at the 2nd hour.

(3) Triglycerides administration, whereas GLUN gives place to a pattern of levels between about the 2nd and the 12th hour.

The highest concentration is attained by the nicotinic acid: it is about two times higher than the peak concentration of niceritrole, 15 times higher than that of sorbinicate, 40 times higher than that of GLUN. Six hours after the administration, the plasma concentration of the free nicotinic acid is about 140 times less than that of the peak for the administration of nicotinic acid, about 80 times less in the case of niceritrole, about 9 times less in the case of sorbinicate, whereas in the case of GLUN the concentration is still within the plateau phase of the nicotinic acid levels.

In order to assess possible differences of activity of the two isomers alpha and beta, as well as of the glucosamine tetranicotinate, the pharmacological tests reported in the table 2 have repeated, and the related results are indicated in the following table 5.

TABLE 5

Effects of the oral administration of the α and β forms of N—nicotinoyl-glucosamine tetranicotinate and of glucosamine tetranicotinate, at a dosage of 100 mg/kg referred to nicotinic acid, on the plasma levels of FFA, tryglicerides cholesterol, and free nitonic acid, in the empty rat.

| | | TIME FROM THE ADMINISTRATION (h) | | | | | | | | | | | |
|---|---|---|---|---|---|---|---|---|---|---|---|---|---|
| | | Percent variations with respect to the control | | | | | | | | Free nicotinic acid μg ml | | | |
| | | FFA | | | TRIGLYCERIDES | | | CHOLESTEROL | | | (average values ± standard error) | | |
| FORM | n | 2 | 4 | 8 | 2 | 4 | 8 | 4 | 8 | 24 | 2 | 4 | 8 | 24 |
| α | 10 | −64 *** | −13 | −7 | −56 * | −68 ** | −47 * | −4 | −12 | −44 *** | 1.18 ±0.13 | 0.68 ±0.28 | 0.66 ±0.27 | 0.26 ±0.11 |
| β | 10 | −67 *** | −30 ** | −44 *** | −53 * | −77 *** | −69 *** | −2 | −17 | −43 *** | 1.58 ±0.37 | 1.29 ±0.34 | 2.28 ±0.52 | 0.11 ±0.03 |
| glucosamine-tetra-nicotinate | 5 | −70 *** | −48 ** | −65 *** | −54 * | −53 *** | −82 ** | −16 | −26 | −59 *** | 2.06 ±0.53 | 0.86 ±0.15 | 2.56 ±0.81 | 0.10 ±0.03 |

\* P < 0.05
\*\* P < 0.01
\*\*\* P < 0.001

All the four substances under test cause the triglycerides to be relevantly reduced, but also in this case the duration of the effect is different in the several groups.

At a dosage of 100 mg/kg, the effect of sorbinicate and niceritrole disappears within the eighth hour, that of the nicotinic acid within the tenth hour, that of GLUN within the twenty fourth hour. At the dose of 30 mg/kg the effect disappears within 2 hours for the sorbinicate and the niceritrole, within 4 hours for the nicotinic acid and within 16 hours for the GLUN.

(4) Cholesterol

At a dosage of 100 mg/kg the nicotinic acid causes the cholestelolemy to be lowered at the eighth, tenth and twenty fourth hour, the sorbinicate at the tenth hour only, whereas the reduction induced by niceritrole is never significant (P 0.10 only at the 24th hour).

GLUN depresses the cholesterolemy from the eighth to the fortyeighth hour. Moreover, the effect of the latter substance seems to be constantly more relevant, from the quantitative point of view, with respect to that of the reference standards.

(5) Plasma levels of free nicotinic acid

Table 4 shows that nicotinic acid, sorbinicate and niceritrole give place to the peak of the plasma concentration of free nicotinic acid within 30 minutes from The preceding results show that the compounds of the invention are endowed with pharmacological and pharmacodynamic properties which render them at least potentially more interesting than nicotinic acid as well as than the derivatives thereof to date available as drugs for the control of the human hyperdislipidemiae.

In fact, the compounds of the invention do not cause the appearance of early and too high levels of nicotinic acid, which are useless from the point of view of the hypolipemizing activity and are the potential cause of a number of side effects (flushing, gastro-intestinal disturbances and some times also hepatic troubles, hyperuricemia, altered tolerability with respect to glucose, strial fibrillations and other arrhythymias) and provide for extended constant plasma levels of free nicotinic acid, which are not much higher than the pharmacologically active concentrations.

As regards the therapeutical use of the compounds of the invention, daily dosages range from 1 to 6 g, the administration taking place in two or three times per day.

As regards the pharmaceutical compositions, the compounds of the invention can be formulated for oral use, in form of coated tablets, pills and capsules, containing 500 to 1000 mg of active compound, together with the standard excipients and carriers.

The following is an example of a pharmaceutical composition of a coated tablets:

| GLUN | mg | 500 |
|---|---|---|
| microgranular cellulose | mg | 35 |
| hydroxyethylmethylcellulose | mg | 6 |
| sodium dioctylisulfosuccinate | mg | 2 |
| carboxymethylstarch | mg | 15 |
| talc | mg | 8 |
| magnesium stearate | mg | 4 |
| lactose | mg | 20.6 |
| titanium dioxide | mg | 4 |
| cellulose acetophtalate | mg | 4.4 |
| diethylphatalate | mg | 1 |

We claim:

1. A nicotinic derivative of glucosamine selected from the group of compounds having the formula:

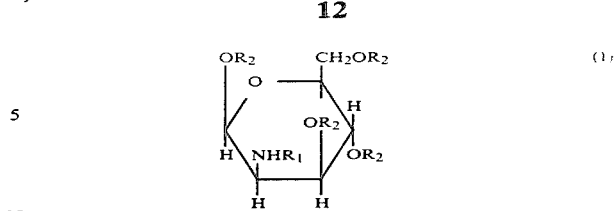

wherein $R_1$ represents H or the radical of nicotinic acid and $R_2$ is the radical of nicotinic acid, and their non toxic, pharmaceutically acceptable acid salts.

2. The derivative of claim 1 being α-N-nicotinoyl-glucosamine tetranicotinate.

3. The derivative of claim 1 being β-N-nicotinoyl-glucosamine tetranicotinate.

4. The derivative of claim 1 being glucosamine tetranicotinate.

5. A composition for lowering the lipid level in plasma and for preventing atheroma formation on vessel walls containing, as the active ingredient, 500 to 1000 mg of a nicotinic derivative of glucosamine according to claim 1, or a salt thereof with a non toxic and pharmaceutically acceptable acid, together with an excipient or inert carrier.

6. Pharmaceutical composition according to claim 5, in form of tablets, pills and capsules.

7. A pharmaceutical composition according to claims 5 or 6 in unit dosage form containing 500 mg of said derivative for administration 2 to 3 times a day.

* * * * *